United States Patent
Krueger et al.

(10) Patent No.: US 8,580,789 B2
(45) Date of Patent: Nov. 12, 2013

(54) TREATING GLAUCOMA

(75) Inventors: Ronald R. Krueger, Cleveland, OH (US); William J. Dupps, Bay Village, OH (US); Stephen Trokel, New York, NY (US); Ivey Thornton, Cleveland, OH (US)

(73) Assignees: The Cleveland Clinic Foundation, Cleveland, OH (US); Stephen Trokel, New York, NY (US)

( * ) Notice: Subject to any disclaimer, the term of this patent is extended or adjusted under 35 U.S.C. 154(b) by 746 days.

(21) Appl. No.: 12/593,720

(22) PCT Filed: Apr. 2, 2008

(86) PCT No.: PCT/US2008/004299
§ 371 (c)(1), (2), (4) Date: Apr. 5, 2010

(87) PCT Pub. No.: WO2008/124009
PCT Pub. Date: Oct. 16, 2008

(65) Prior Publication Data
US 2010/0189817 A1    Jul. 29, 2010

Related U.S. Application Data

(60) Provisional application No. 60/921,317, filed on Apr. 2, 2007.

(51) Int. Cl.
*A61K 31/525* (2006.01)
*A61K 31/11* (2006.01)

(52) U.S. Cl.
USPC ............ 514/251; 514/705; 514/912; 514/913

(58) Field of Classification Search
USPC ................................. 514/251, 705, 912, 913
See application file for complete search history.

(56) References Cited

U.S. PATENT DOCUMENTS

| | | | |
|---|---|---|---|
| 7,727,544 B2 | 6/2010 | Schwartz et al. | |
| 2005/0271590 A1 | 12/2005 | Schwartz et al. | |
| 2008/0114283 A1 | 5/2008 | Mattson et al. | |

FOREIGN PATENT DOCUMENTS

| | | |
|---|---|---|
| WO | WO 2005/110397 A1 | 11/2005 |
| WO | WO 2006/060547 A2 | 6/2006 |

(Continued)

OTHER PUBLICATIONS

Krueger et al., How might corneal elasticity help us understand diabetes and intraocular pressure?, J Refract Surg. Jan. 2007;23(1):85-8.*

(Continued)

*Primary Examiner* — Gigi Huang
(74) *Attorney, Agent, or Firm* — Hamilton, Brook, Smith & Reynolds, P.C.

(57) ABSTRACT

Provided herein are methods of protecting all or a portion of the optic nerve fiber layer within the optic nerve/lamina cribrosa (ONLC) complex in an individual in need thereof, comprising administering to the individual a therapeutically effective amount of an agent that results in crosslinking of collagen in the indiviudal's peripapillary sclera, thereby stiffening the individual's peripapillary sclera and protecting all or a portion of the optic nerve fiber layer within the ONLC of the individual. In a particular embodiment, the invention is directed to methods of treating glaucoma in an individual in need thereof, comprising administering to the individual a therapeutically effective amount of an agent that results in crosslinking of collagen in the indiviudal's peripapillary sclera, thereby stiffening the individual's peripapillary sclera and treating the glaucoma in the individual. In yet another embodiment, the invention is directed to methods of treating glaucomatous optic neuropathy in an individual in need thereof, comprising administering to the individual a therapeutically effective amount of an agent that results in crosslinking of collagen in the indiviudal's peripapillary sclera, thereby stiffening the individual's peripapillary sclera and treating the glaucomatous optic neuropathy in the individual. The method can further comprise administering to the individual a therapeutically effective amount of an agent that results in crosslinking of collagen in the indiviudal's lamina cribrosa (LC).

9 Claims, 5 Drawing Sheets

Normal optic nerve anatomy with lamina cribrosa bordered in black and the black arrows specifying where peripapillary scleral crosslinking is performed. (Modified from Jonas, et al[13])

(56) References Cited

FOREIGN PATENT DOCUMENTS

| WO | WO 2008/070185 A2 | 6/2008 |
|---|---|---|
| WO | WO 2008/124009 A2 | 10/2008 |

OTHER PUBLICATIONS

Newman, Hereditary Optic Neuropathies: From the Mitochondria to the Optic Nerve, Sep. 2005, American Journal of Ophthalmology, 140, 517-523.*
Moss, Leber's Congenital Amaurosis, http://www.tsbvi.edu/Outreach/seehear/spring01/lebers.htm, printed Apr. 27, 2008, 3 pages.*
Andreassen, T.T., et al., "Biomechanical Properties of Keratoconus and Normal Corneas," *Exp. Eye Res.* 31:435-441 (1980).
Avery, N.C., et al., "The Effects of the Maillard Reaction on the Physical Properties and Cell Interactions of Collagen," *Pathologie Biologie* 54:387-395 (2006).
Bailey, A.J., "Structure, Function and Ageing of the Collagens of the Eye," *Eye 1*:175-183 (1987).
Bellezza, A.J., et al., "Deformation of the Lamina Cribrosa and Anterior Scleral Canal Wall in Early Experimental Glaucoma," *Invest Opthamol & Vis Sci.* 44(2):623-637 (2003).
Braunstein, R.E., et al., "Endoscopy and Biopsy of the Orbit," *Ophthalmic Plastic and Reconstructive Surgery* 11(4):269-272 (1995).
Burgoyne, C.F., et al., "The Optic Nerve Head as a Biomechanical Structure: a New Paradigm for Understanding the Role of IOP-related Stress and Strain in the Pathophysiology of Glaucomatous Optic and Nerve Head Damage," *Retinal and Eye Research* 24:39-73 (2005).
Burgoyne, C.F., et al., "Three-Dimensional Reconstruction of Normal and Early Glaucoma Monkey Optic Nerve Head Connective Tissues," *Invest Ophthamol Vic Sci.* 45:4388-4399 (2004).
Congdon, N.G., et al., "Central Corneal Thickness and Corneal Hysteresis Associated with Glaucoma Damage," *Am J Ophthalmol* 141:868-875 (2006).
Davis, B.R., et al., "Age-dependent Changes in the Shear Wave Propagation Through Human Skin," *Experimental Gerontology* 24:201-210 (1989).
Downs J.C., et al., "Three-dimensional Histomorphometry of the Normal and Early Glaucomatous Monkey Optic Nerve Head: Neural Canal and Subarachnoid Space Architecture," *Invest Ophthalmol Vis Sci.* 48:3195-3208 (2007).
Downs, J.C., et al., "Viscoelastic Material Properties of the Peripapillary Sclera in Normal and Early-Glaucoma Monkey Eyes," *Invest Ophthalmol Vis Sci.* 46:540-546 (2005).
Dupps, Jr., W.J. MD, PhD, et al., "Surface Wave Elastometry of the Cornea in Porcine and Human Donor Eyes," *J. Refract Surg* 23(1):66-75 (2007).
Eid, T.E., et al., "Quantitative Differences Between the Optic Nerve Head and Peripapillary Retina in Low-tension and High-tension Primary Open-angle Glaucoma," *American Journal of Ophthalmology* 124:805-813 (1997).
Friedman, D.S. MD, et al., "An Evidence-based Assessment of Risk Factors for the Progression of Ocular Hypertension and Glaucoma," *Am J Ophthalmol* 138:S19-S31 (2004).
Gordon, M.O. PhD, et al., "The Ocular Hypertension Treatment Study," *Arch Ophthalmol* 120:714-720 (2002).
Gorodetsky, R. Ph.D., et al., "Late Effects of Dose Fractionation of the Mechanical Properties of Breast Skin Following Post-lumpectomy Radiotherapy," *Int. J. Radiation Oncology Biol. Phys.* 45(4): 893-900 (1999).
Girton, T.S., et al., "Exploiting Glycation to Stiffen and Strengthen Tissue Equivalents for Tissue Engineering," *J Biomed Mater Res* 46:87-92 (1999).
Hupp, S.L. MD, et al., "Optic Nerve Sheath Decompression Review of 17 Cases," *Arch Ophthalmol* 105:386-389 (1987).
Igaki, N., et al., "Effects of 3-Deoxyglucosone on the Maillard Reaction," *Clin. Chem* 36(4):631-634 (1990).

Jonas, J.B., et al., "Anatomic Relationship Between Lamina Cribrosa, Intraocular Space, and Cerebrospinal Fluid Space," *Invest Ophthalmol Vis Sci.* 44:5189-5195 (2003).
Kikuchi, S., et al., "Neurotoxocity of Methylglyoxal and 3-Deoxyglucosone on Cultured Cortical Neurons: Synergims Between Glycation and Oxidative Stress, Possibly Involved in Neurodegenerative Diseases," *Journal of Neuroscience Research* 57:280-289 (1999).
Krueger, R.R. MD, et al., "How Might Corneal Elasticity Help us Understand Diabetes and Intraocular Pressure?," *Journal of Refractive Surgery* 23:85-88 (2007).
Kuo, I.C. MD, et al., "Is There an Association Between Diabetes and Keratoconus?," *Ophthalmology* 113:184-190 (2006).
Miglior, S. MD, "Results of the European Glaucoma Prevention Study," *Ophthalmology* 112:366-375 (2005).
Myles, M.E., et al., "Recent Progress in Ocular Drug Delivery for Posterior Segment Disease: Emphasis on Transscleral Iontophoresis," *Advanced Drug Delivery Reviews* 57:2063-2079 (2005).
Neufeld, A.H., "Pharmacologic Neuroprotection with an Inhibitor of Nitric Oxide Synthase for the Treatment of Glaucoma," *Brain Research Bulletin* 62:455-459 (2004).
Olsen, T.W., et al., "Porcine Sclera: Thickness and Surface Area," *Invest Ophthalmol Vis Sci.* 43:2529-2532 (2002).
Paik, D.C., et al., "Initial Studies as Nitrite as a Topical Stiffening Agent for Cornco-Scleral Disorders," *ARVO Abstract #4023* (2007).
Pereira, J.M., et al., "Analysis of Shear Wave Propagation in Skin; Application to an Experimental Procedure," *J. Biomechanics* 23(8):745-751 (1990).
Pierscionek, B.K., et al., "The Effect of Changing Intraocular Pressure on the Corneal and Scleral Curvatures in the Fresh Porcine Eye," *Br J Ophthalmol* 91:801-803 (2007).
Poonja, S. BS, et al., "Dynamic Visual Stimulus Presentation in an Adaptive Optics Scanning Laser Ophthalmoscope," *Journal of Refractive Surgery* 21:S575-S580 (2005).
Potts, R.O., Ph,D., et al., "Changes with Age in the Moisture Content of Human Skin," *The Journal of Investigative Dermatology* 82(1):97-100 (1984).
Potts, R.O., et al., "The Dynamic Mechanical Properties of Human Skin In Vivo," *J. Biomechanics* 16(6):365-372 (1983).
Prabhakaran, V.C., et al., "Orbital Endoscopic Surgery," *Indian J Ophthamol* 56:5-8 (2008).
Qian, Y., et al., "Comparative Study of UVA Riboflavin Crosslinking and "Flash-linking" Using Surface Wave Elastometry," *Oasis Abstract #3361/A179* (2008).
Quigley, H.A., et al., "The Number of People with Glaucoma Worldwide in 2010 and 2020," *Br J Ophthalmol* 90:262-267 (2006).
Resch, H., et al., "Topical Drug Therapy in Glaucoma," *Wien Med Wochenschr* 156(17-18):501-507 (2006).
Sander, E.A., et al., "A Cellular Solid Model of the Lamina Cribrosa: Mechanical Dependence on Morphology," *Journal of Biomechanical Engineering* 128:879-889 (2006).
Seiler, T., et al., "Manifest Diabetes and Keratoconus: A Retrospective Case-control Study," *Graefe's Arch Clin Exp Ophthalmol* 238:822-825 (2000).
Sigal, I.A., et al., "Factors Influencing Optic Nerve Head Biomechanics," *Invest Ophthalmol Vis Sci.* 46:4189-4199 (2005).
Sigal, I.A., et al., "Finite Element Modeling of Optic Nerve Head Biomechanics," *Invest Ophthalmol Vis Sci.* 45:4378-4387 (2004).
Spoerl, E., PhD et al., "Techniques for Stiffening the Cornea," *J Refract Surg* 15:711-713 (1999).
Spoerl, E., et al., "The Influence of Various Substances on the Biomechanical Behavior of Lamina Cribrosa and Peripapillary Sclera," *Invest Ophthalmol Vis Sci.* 46:1286-1290 (2005).
Thornton, I.L., et al., "Biomechanical Effects of Intraocular Pressure Elevation on Optic Nerve/Lamina Cribrosa Before and After Peripapillary Scleral Collagen Cross-linking," *Invest Ophthalmol Vis Sci.* 50:1227-1233 (2009).
Thorpe, S.R., et al., "Role of the Maillard Reaction in Diabetes Mellitus and Diseases of Aging," *Drugs & Aging* 9(2):69-77 (1996).

(56) References Cited

OTHER PUBLICATIONS

Vexler, A., et al., "Evaluation of Skin Viscoelasticity and Anisotropy by Measurement of Speed of Shear Wave Propagation with Viscoelasticity Skin Analyzer," *J Invest Dermatol 113*:732-739 (1999).

Wang, Y. BS, et al., "Iontophoresis of Indocyanine Green and Monastral Blue B for Gonioscopic Diode Laser Sclerectomy," *Ophthalmic Surg Letters 27*:484-487 (1996).

Wollensak, G. MD, et al., "Collagen Crosslinking of Human and Porcine Sclera," *J Cataract Refract Surg 30*:689-695 (2004).

Wollensak, G., et al., "Cross-linking of Scleral Collagen in the Rabbit Using Riboflavin and UVA," *Acta Ophthalmol. Scand. 83*:477-482 (2005).

Wollensak, G., et al., "Influence of Indocyanine Green Staining on the Biomechanical Strength of Porcine Internal Limiting Membrane," *Opthalmologica 218*:278-282 (2004).

Wollensak, G. MD, et al., "Riboflavin/Ultraviolet-A-induced Collagen Crosslinking for the Treatment of Keratoconus," *Am J Ophthalmol 135*:620-627 (2003).

Yang, H., et al., "3-D Histomorphometry of the Normal and Early Glaucomatous Monkey Optic Nerve Head: Lamina Cribrosa and Peripapillary Scleral Position and Thickness," *Invest Ophthalmol Vis Sci. 48*:4597-4607 (2007).

Burgoyne C.F., et al., "The Optic Nerve Head as a Biomechanical Structure: A New Paradigm for Understanding the Role of IOP-Related Stress and Strain in the Pathophysiology of Glaucomatous Optic Nerve Head Damage", *Prog. Retin Eye Res.*, 24(1):39-73 (Jan. 2005).

Girton T.S., et al., "Confined Compression of a Tissue-Equivalent: Collagen Fibril and Cell Alignment in Response to Anisotropic Strain", *Biomech, Eng.*, 124(5):568-75 (Oct. 2002).

Rocha, Kam., et al., "Comparative Study of Riboflavin-UVA Cross-Linking and "Flash-Linking" Using Surface Wave Elastometry", *J Refract. Surg.*, 24(7): S748-S751 (Sep. 2008).

Oct. 22, 2008, International Search Report, PCT/US2008/004299.

Oct. 22, 2008, Written Opinion of the International Searching Authority, PCT/US2008/004299.

Oct. 15, 2009, International Preliminary Report on Patentability, PCT/US2008/004299.

\* cited by examiner

Figure 1: Normal optic nerve anatomy with lamina cribrosa bordered in black and the black arrows specifying where peripapillary scleral crosslinking is performed. (Modified from Jonas, et al[13])

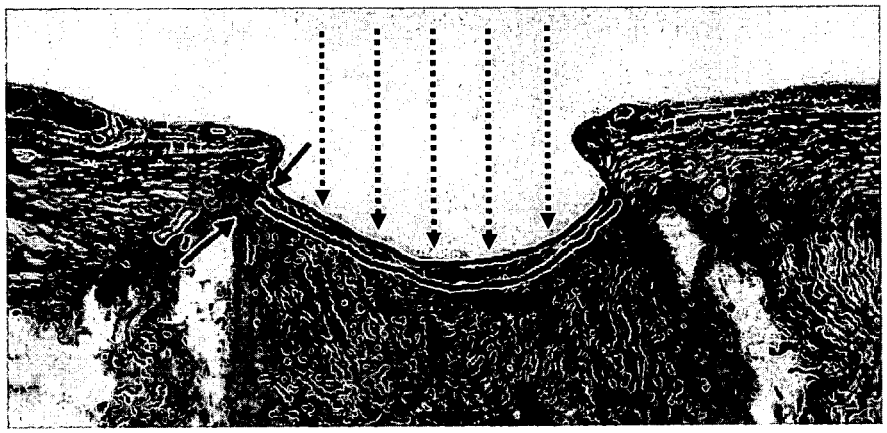

Figure 2: Advanced glaucomatous optic nerve anatomy with a thinned, posteriorly deformed LC, bordered in black. The dashed arrows specify both the location for intravitreal application of the crosslinking agent and the pinpoint delivery of light to the LC. The black arrows specify the close proximity of the intrathecal space to the LC and peripapillary canal wall. (Modified from Jonas et al[13])

Figure 2

Figure 3a (left)- Exposed Optic Nerve/Lamina Cribrosa Complex after transecting the Optic Nerve with a Surgical Blade; Figure 3b (right)- Magnification of Figure 3a shows exposed Lamina Cribrosa Figure 4- In-Line Pressure Transducer Infused with Normal Saline for Direct Intraocular Pressure Control Figure 5- Surface Wave Velocity Measurements were taken between 2 Points using the Sonic Eye Elastometer atop the Optic Nerve/Lamina Cribrosa Complex (area 1) and the Peripapillary Sclera (area 2 & 3). Note the fiducial marks placed immediately adjacent to the Optic Nerve/Laminal Cribrosa Complex in group 3 eyes.

TREATING GLAUCOMA

RELATED APPLICATIONS

This application is the U.S. National Stage of International Application No. PCT/US2008/004299, filed Apr. 2, 2008, which designates the U.S., published in English, and claims the benefit of U.S. Provisional Application No. 60/921,317, filed on Apr. 2, 2007. The entire teachings of the above applications are incorporated herein by reference.

GOVERNMENT SUPPORT

The invention was supported, in whole or in part, by a grant NIH 8K12 RR023264 from the National Institutes of Health. The Government has certain rights in the invention.

BACKGROUND OF THE INVENTION

Glaucoma is among the leading causes of blindness in the United States and worldwide. It is estimated that more than 2.5 million people in the United States have glaucoma and that more than 130,000 people are legally blind from the disease (Gordon M O, et al., *Arch Opthalmol;* 120(6):714-720 (2002)). By the year 2010, the estimated worldwide prevalence of glaucoma will be 60 million, with 4.5 million being legally blind (Quigley H A, et al., *Br J Opthalmol.;* 90(3):262-267 (2006)). Glaucoma is commonly associated with the presence of high intraocular pressure (IOP), optic nerve damage and patterned visual field loss, but many other risk factors for glaucomatous optic neuropathy have been identified (Gordon M O, et al., *Arch Opthalmol;* 120(6):714-720 (2002)). In a recent review of the Ocular Hypertension Treatment Study, the most significant risk factors for the development of glaucoma included age, IOP, cup/disc ratio and thin central corneal thickness, where the latter remained an important predictor in both univariate and multivariate analyses (Gordon M O, et al., *Arch Opthalmol;* 120(6):714-720 (2002)). This latter finding has generated increased interest in the biomechanical properties of the ocular coat and its role in the pathophysiology of glaucoma.

In studies such as the Ocular Hypertension Treatment Study and the European Glaucoma Prevention Study, evidence suggests that a history of diabetes mellitus is inversely associated with glaucoma risk (Gordon M O, et al., *Arch Opthalmol;* 120(6):714-720 (2002); Miglior S, et al., *Opthalmology;* 112(9):366-375 (2005)) and may therefore be protective. Hyperglycemia is associated with a naturally occurring form of collagen crosslinking resulting from non-enzymatic glycation of proteins that leads to tissue stiffening (Thorpe S R, et al., *Drugs & Aging;* 9(2):69-77 (1996)). Computational simulations have suggested that mechanical strain in prelaminar optic nerve tissue, a potential mechanism of injury in glaucomatous optic neuropathy, is greatest as a function of IOP when peripapillary scleral stiffness is lowest (Sigal I A, et al., *Invest Opthalmol Vis Sci.;* 46(11):4189-4199 (2005)).

Improved therapies and preventive interventions for glaucoma are needed.

SUMMARY OF THE INVENTION

As described herein, natural crosslinking of collagen in the lamina cribrosa or peripapillary sclera contributes to the protective effects of diabetes mellitus against glaucoma. In the anterior segment, similar effects in corneal collagen may account for the protective effect of diabetes in keratoconus (Seiler T, et al., *Graefes Arch Clin Exp Opthalmol;* 238(10):822-825 (2000); Kuo I C, et al., *Opthalmology;* 113(2):184-190 (2006)) a disease characterized by abnormal corneal elasticity (Andreassen T T, et al., *Exp Eye Res.;* 31(4):435-441 (1980)) and progressive instability of corneal shape. Collagen crosslinking has been introduced as a technique for stiffening the cornea (Spoerl E, Seiler T. *J Refract Surg;* 15(6):711-713 (1999)), and clinically, topical riboflavin coupled with ultraviolet-A (UVA) light exposure, has been used effectively as a stabilizing treatment for keratoconus (Wollensak G, et al., *Am J Opthalmol.;* 135(5):620-627 (2003)).

Shown herein is that collagen crosslinking of the lamina cribrosa and/or peripapillary sclera provides a method for modulating biomechanical stress and strain-based injury mechanisms in the laminar region toward the goal of preventing the onset or slowing the progression of glaucomatous optic neuropathy. Recent experiments have demonstrated that direct application of crosslinking agents such as glyceraldehyde and methylglyoxal to the lamina cribrosa and peripapillary sclera can increase the tensile strength of these structures in explants subjected to extensiometric analysis (Spoerl E, et al., *Invest Opthalmol Vis Sci.;* 46(4):1286-1290 (2005)). As described herein, the in situ optic nerve/lamina cribrosa complex (ON/LC) and/or the peripapillary sclera (PS) of porcine globes was crosslinked using riboflavin/UVA and glutaraldehyde (GTA), a dialdehyde which is a potent positive control for crosslinking effects (Spoerl E, Seiler T. *J Refract Surg;* 15(6):711-713 (1999)). Local stiffness and deformation in the ON/LC and PS regions were measured before crosslinking at low and high intraocular pressures to 1) measure the regional strain and stiffness changes generated during an IOP increase, then again after crosslinking to 2) assess the degree of crosslinking achieved under constant IOP and 3) study the potential protective effect of ON/LC and/or PS crosslinking against ON/LC stiffening and strain during an IOP increase.

Accordingly, the invention is directed to methods of protecting (e.g., inhibiting injury to or loss of) all or a portion of the optic nerve fiber layer within or contiguous with the optic nerve/lamina cribrosa complex in an individual in need thereof, comprising administering to the individual a therapeutically effective amount of an agent that results in crosslinking of collagen in the individual's peripapillary sclera, thereby stiffening the individual's peripapillary sclera and protecting all or a portion of the optic nerve fiber layer within or contiguous with the optic nerve/lamina cribrosa complex of the individual.

In a particular embodiment, the invention is directed to methods of treating glaucoma in an individual in need thereof, comprising administering to the individual a therapeutically effective amount of an agent that results in crosslinking of collagen in the indiviudal's peripapillary sclera, thereby stiffening the individual's peripapillary sclera and treating the glaucoma in the individual.

In yet another embodiment, the invention is directed to methods of treating glaucomatous optic neuropathy in an individual in need thereof, comprising administering to the individual a therapeutically effective amount of an agent that results in crosslinking of collagen in the indiviudal's peripapillary sclera, thereby stiffening the individual's peripapillary sclera and treating the glaucomatous optic neuropathy in the individual.

The methods described herein can further comprise administering to the individual a therapeutically effective amount of an agent that results in crosslinking of collagen in and around the indiviudal's lamina cribrosa.

In the methods of the invention, stiffness of the peripapillary sclera increases from about 1.2-fold to about 50-fold after contact with the agent. In a particular embodiment, the stiffness of the peripapillary sclera increases about 20-fold after contact with the agent. Hence, with an increase in the stress of intraocular pressure, the lamina and ring of sclera around it are unlikely to undergo the same degree of strain after peripapillary scleral crosslinking than that experienced before.

In some embodiments, the individual has normal intraocular pressure (less than 21 mmHg). In other embodiments, the individual has high intraocular pressure (greater than 21 mmHg).

Agents for use in the methods of the invention include a photosensitizer crosslinking agent (e.g., riboflavin or other photosensitizing agent) and light (e.g., UV light, blue light, ambient light, a chemical fixative crosslinking agent (e.g., glutaraldehyde), a glycation-induced crosslinking agent (e.g., methylglyoxal, glyceraldehyde or a β-nitro alcohol compound) or a combination thereof.

BRIEF DESCRIPTION OF THE DRAWINGS

FIG. 2 shows advanced glaucomatous optic nerve anatomy with a thinned, posteriorly deformed LC, bordered in black. The dashed arrows specify both the location for intravitreal application of the crosslinking agent and the pinpoint delivery of light to the LC. The black arrows specify the close proximity of the intrathecal space to the LC and peripapillary canal wall. (Modified from Jonas J B, et al., *Invest Opthalmol Vis Sci;* 44: 5189-5195 (2003)).

DETAILED DESCRIPTION OF THE INVENTION

Figure 1:
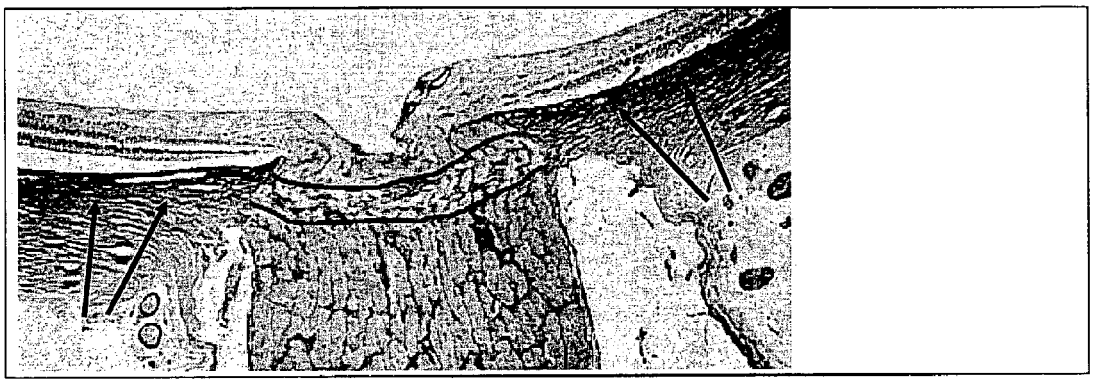
FIG. 1 shows normal optic nerve anatomy with lamina cribrosa bordered in black and the black arrows specifying where peripapillary scleral crosslinking is performed. (Modified from Jonas J B, et al., *Invest Opthalmol Vis Sci;* 44: 5189-5195 (2003)).

Glaucomatous optic atrophy is a common disorder that has multiple risk factors and no widely accepted therapy, except that of lowering the intraocular pressure (IOP). The primary pathology of glaucoma, however, is not elevated intraocular pressure, but rather a progressive loss of optic nerve fiber layer within the optic nerve/lamina cribrosa complex (ON/LC). Although elevated intraocular pressure is a prominent risk factor for glaucomatous damage, resilience of the optic nerve against abnormally high pressures is noted in some eyes with ocular hypertension, while other eyes show focal, progressive damage even with low or normal IOP (Eid T E, et al., *Am J Opthalmol.;* 124(6):805-813 (1997)).

It is believed that the collagen based and connective tissue structures within (i.e., lamina cribrosa) and around the optic nerve (i.e., peripapillary sclera) provide structural support to the ganglion cell axons as they traverse the fenestrated meshwork of the lamina cribrosa within the optic nerve head. The lamina cribrosa (LC) itself is contiguous with and anchored to the peripapillary scleral (PS) within the 2.0 mm diameter opening (canal) of the inner ⅓ of the scleral collagen fibers. The outer ⅔ fibers are contiguous with the dural sheath of the optic nerve, creating an outer opening of 3.5 mm. While these anatomical relationships have been understood for some time, the biomechanical properties of these structures and their relevance to glaucoma have only more recently been investigated experimentally. Major contributions have been made in the biomechanical characterization of the ON/LC and peripapillary sclera in monkey eyes with early induced glaucoma. Confocal scanning laser tomography (CSLT) has been used to demonstrate that normal compliance of the lamina cribrosa at low IOP is acutely altered when IOP is increased as the lamina becomes hyper-compliant and displaces posteriorly (Bellezza A J, et al. *Invest Opthalmol Vis Sci.;* 44(2):623-637 (2003)). With chronic IOP elevation and induced glaucoma, the lamina not only further displaces posteriorly (8 times more than with high IOP only), but the laminar thickness and the scleral canal diameter increases as well (hyper-compliant and plastic deformation). This permanent posterior deformation and expansion of the anterior and posterior scleral canal openings in glaucomatous monkey eyes has been verified by three dimensional reconstructions of serially sectioned optic nerve head samples embedded in paraffin (Burgoyne C F, et al., *Invest Opthalmol Vis Sci.;* 45(12):4388-4399 (2004)). In subsequent viscoelastic tensile testing of peripapillary scleral explants, the sclera within and around the scleral canal wall revealed higher equilibrium moduli and thus greater stiffness in eyes with early induced glaucoma (7.46±1.58 MPa) than in normal eyes (4.94±1.22 MPa) (Downs J C, et al., *Invest Opthalmol Vis Sci;* 46(2):540-546 (2005)). Because these were studies of induced glaucoma and not of disease predisposition, stiffening of peripapillary sclera is likely to represent a compensatory response involving an attempt by the extracellular matrix to resist the increased stress and strain imposed by elevated IOP. Within a conceptual framework where IOP-related connective tissue stress and strain mediate and predict the onset and progression of glaucomatous axonal insult, alteration of peripapillary scleral compliance may represent an innate form of neuroprotection.

Finite element modeling (FEM) of the optic nerve head and surrounding structures predicts that the lamina cribrosa strains 4 to 5.5% on average (max 7.7%) under an IOP increase to 50 mmHg (similar to the findings described herein), and that the magnitude of strain is determined primarily by the peripapillary scleral stiffness, and then less so by its thickness, optic canal diameter, the lamina cribrosa stiffness, and optic cup shape (Sigal I A, et al., *Invest Opthalmol Vis Sci;* 45(12):4378-4387 (2004)). In fact, a subsequent FEM analysis of factors influencing optic nerve head biomechanics suggests scleral stiffness has the greatest impact, followed by the radius of the eye, the stiffness of the lamina cribrosa, the intraocular pressure and the thickness of the scleral shell (Sigal I A, et al., *Invest Opthalmol Vis Sci.;* 46(11):4189-4199 (2005)). Both cup depth and cup to disc ratio had the least impact, suggesting that acute deformation and strain of the optic nerve head and corresponding neural tissue may be less dependent on the IOP's direct effect on the optic nerve head than on its indirect effects mediated by the sclera.

Described herein are experiments investigating whether stiffening of the peripapillary sclera can be achieved using a therapeutic collagen crosslinking method to enhance the natural compensation of pathophysiological mechanisms associated with glaucoma either at 1) an early stage prior to significant scleral canal wall expansion and/or posterior deformation of the lamina cribrosa, or at 2) the later, more advanced stage. While advancing age is a known risk factor for glaucoma (Friedman D S, et al., *Am J Opthalmol;* 138(3 Suppl):S19-31 (2004)), the general phenomenon of natural crosslinking of ocular collagen with age (Bailey A J. *Eye;* 1(Pt 2):175-183 (1987)) does not necessarily implicate collagen stiffening as a risk factor for glaucoma. On the contrary, current models of biomechanical injury in glaucoma support our postulate that this phenomenon may instead reduce predisposition for glaucomatous optic neuropathy by enhancing the biomechanical resilience of the peripapillary sclera and lamina cribrosa. It is possible that other age-related declines in vascular, neuronal and aqueous outflow function counteract this paradoxical benefit of aging and lead to the well-known associations between age and glaucoma risk. Diabetes mellitus without vasculopathy has also been associated with a protective effect in the onset and progression of glaucoma in several studies, and this further supports the contention that tissue stiffening can have protective effects (Krueger R R, et al., *J Refract Surg.;* 23:85-88 (2007)). Further research on the specific localization of crosslinking effects in ocular tissues during aging and diabetic non-enzymatic glycation, particularly in the optic nerve head region, will be important for better understanding of these relationships.

Our own data (Thornton, I L., et al., *Invest. Opthalmol. Vis. Sci.;* in review) provides non-destructive measurements of stiffness at the posterior globe, and provides elastic moduli consistent with prior studies in excised porcine scleral (0.3 MPa) and lamina cribrosa (0.1 MPa) explants (Spoerl E, et al., *Invest Opthalmol Vis Sci.;* 46(4):1286-1290 (2005)), indicating that the PS is indeed significantly stiffer than the LC. Although the estimate of 836 kPa for the native elastic modulus is limited by the simplifying assumptions of uniform, isotropic material properties, spherical geometry, and uniform scleral thickness, this value is in line with the work of Pierscionek B K, et al., *Br J Opthalmol.;* 91(6):801-803 (2007) whose modulus of 500 kPa was derived over a lower range of pressures and incorporated the entire scleral circumference, which includes regions that are much thinner and presumably less stiff than the posterior pole (Olsen T W, et al., *Invest Opthalmol Vis Sci;* 43(8):2529-2532 (2002)). The estimates of the change in elastic modulus of peripapillary sclera with glutaraldehyde-mediated crosslinking suggest a nearly 20-fold increase in stiffness, about double the effect observed by Spoerl et al with glutaraldehyde in the cornea (Spoerl E, Seiler T. *J Refract Surg.;* 15(6):711-713 (1999)). While these measurements are specific to the porcine species and absolute values can be affected by dehydration artifact, similar measurements of in situ properties in human sclera may be of great value in future efforts to model the relationship between ON/LC and PS properties.

Another major conclusion of our work is that IOP elevation measurably increases the in situ stiffness of the ON/LC and PS and is accompanied by circumferential strain in both regions. Both mechanisms are likely important in the pathogenesis and progression of glaucomatous optic neuropathy. Furthermore, collagen crosslinking of the PS measurably stiffens the PS and shields the ON/LC from further stiffening and circumferential strain during IOP elevation. Stiffening of the ON/LC was unique to one group (i.e., Group 3 in Example 3) and is probably related to that fact that surface wave velocity was lower at the sub-physiologic pressures (2-4 mmHg) used in this group than in groups tested at 10 mmHg and higher (Table 1). A shift from very high compliance to lower compliance as the collagen fibrils of the ocular coat become taut with the stress of inflation will result in a higher effective elastic modulus (approximated by the local slope of the curve). For similar reasons, the ON/LC may be more heavily impacted by stiffening of the surrounding scleral ring, which may reduce the flaccidity of the entire region in this very low pressure range and increase the effective stiffness of adjacent structures. These observations indicate that the range of pressures investigated is an important consideration and that the effects of PS stiffening on ON/LC stiffness and strain behavior should be explored over several different ranges of IOP. Laminar stress is a function of both IOP and peripapillary scleral properties, and it is likely that a combination of traditional treatment paradigms for IOP control and modulation of peripapillary scleral properties provides the most powerful approach to altering the forces of injury in at-risk patients.

Inter-individual differences in scleral stiffness is likely a significant and, as contended herein, a modifiable risk factor for glaucomatous optic neuropathy. Such differences may have more impact than the relatively small changes in scleral stiffness one might expect from the oxidative effects of tissue aging. Indeed, FEM simulations by Sigal et al suggest that while strain behavior in the prelaminar optic nerve is a complex function of scleral stiffness, strain increases almost exponentially when scleral stiffness decreases within the lowest range of simulate values (Sigal I A, et al., *Invest Opthalmol Vis Sci;* 46(11):4189-4199 (2005)). Thus, it is possible that those patients with very low peripapillary scleral stiffness are at dramatically increased risk of neuronal injury even at physiological IOP, and comprise some of the clinical population of patients known to have normal tension glaucoma. Abnormalities of scleral collagen stiffness may be reflected to some degree in other anatomic or functional ocular measurements, and such abnormalities may account in part for the associations of low central corneal thickness (Gordon, M O, et al., *Arch. Opthalmol,* 120(6):714-420 (2006)) and low corneal hysteresis (Congdon N G, et al., *Am J Opthalmol.;* 141 (5):868-875 (2006)) with glaucoma progression.

In the experiments described herein using whole porcine globes, and measuring the surface wave velocity (Dupps W J Jr, et al., *J Refract Surg.;* 23(1):66-75 (2007)) of PS and LC under both low and raised intraocular pressure, riboflavin/UVA and glutaraldehyde were used as the agents for crosslinking because of the their ready availability and shorter exposure time requirements. Extrapolating from histomorphologic observations of early induced glaucoma in primates and computational models (Sigal I A, et al., *Invest Opthalmol Vis Sci;* 46(11):4189-4199 (2005); Burgoyne C F, et al., *Prog Retin Eye Res.;* 24(1):39-73 (2005)), increasing peripapillary scleral stiffness likely provides a protective effect against ON/LC deformation and radial strain. The efforts used herein in crosslinking of the peripapillary sclera verify this biomechanical benefit, both with surface wave elastometry, and in particular with a notable reduction of ON/LC and PS strain.

Provided herein are methods of protecting (e.g., inhibiting loss of) all or a portion of the optic nerve fiber layer within the optic nerve/lamina cribrosa (ONLC) complex in an individual in need thereof, comprising administering to the individual a therapeutically effective amount of an agent that results in crosslinking of collagen in the indiviudal's peripapillary sclera, which surrounds and is intimately connected with the lamina cribrosa, thereby stiffening the individual's peripapillary sclera and protecting all or a portion of the optic nerve fiber layer within or contiguous with the ONLC of the individual (so as to protect the ganglion cell nerve fibers treaversing through the lamina cribrosa).

In a particular embodiment, the invention is directed to methods of treating glaucoma in an individual in need thereof, comprising administering to the individual a therapeutically effective amount of an agent that results in crosslinking of collagen in the indiviudal's peripapillary sclera, which surrounds and is intimately connected with the lamina cribrosa, thereby stiffening the individual's peripapillary sclera and treating the glaucoma in the individual.

In yet another embodiment, the invention is directed to methods of treating glaucomatous optic neuropathy in an individual in need thereof, comprising administering to the individual a therapeutically effective amount of an agent that results in crosslinking of collagen in the indiviudal's peripapillary sclera, which surrounds and is intimately connected with the lamina cribrosa, thereby stiffening the individual's peripapillary sclera and treating the glaucomatous optic neuropathy in the individual.

The method can further comprise administering to the individual a therapeutically effective amount of an agent that results in crosslinking of collagen in and around the indiviudal's lamina cribrosa (LC).

In the methods provided herein, an agent that results in crosslinking of collagen in the indiviudal's peripapillary sclera and/or lamina cribrosa is administered to an individual. A variety of suitable crosslinking agents that can be used in the methods are known in the art. For example, in determining the optimal methods for therapeutic crosslinking, Spoerl et al. summarized various techniques for crosslinking the cornea. Such agents can be used in the methods provided herein, and generally fall into 3 categories: 1) a photosensitizer plus light, 2) chemical fixative agents and 3) glycation-induced crosslinking with aldehyde sugars (Spoerl E, Seiler T. *J Refract Surg.*; 15(6):711-713 (1999)). The former category has been successfully used clinically in the form of topical riboflavin 0.1% and UV light at 365 nm for stabilizing corneal shape in keratoconus (Wollensak G, et al., *Am J Opthalmol.*; 135(5):620-627 (2003)). The middle category, although representative of the strongest crosslinkers, such as glutaraldehyde used in our study, deals with agents that are generally toxic to ocular tissues. The latter category, which involves nonenzymatic glycation, is the least damaging to cellular structures, maintaining good cell viability without eliciting inflammation (Girton T S, et al., *J Biomed Mater Res.*; 60(1): 87-92 (1999)). There are several glycation-induced crosslinking agents which could be used for crosslinking posterior and peripapillary scleral collagen (ie. methylglyoxal, glyceraldehydes, etc) (Spoerl E, et al., *Invest Opthalmol Vis Sci.*; 46(4): 1286-1290 (2005)).

In studying the relative efficacy of therapeutic crosslinking in human and porcine sclera, Wollensak and Spoerl have determined the three most effective agents as glutaraldehyde, glyceraldehydes and riboflavin/UVA irradiation with a rise in porcine scleral stress (rigidity) of 8×, 5× and 1.5× and human scleral stress (rigidity) of 122%, 34% and 29%, respectively (Wollensak G, et al., *J Cataract Refract Surg.*; 30(3):689-695 (2004)). The length of time for crosslinking of parallel scleral strips exposed to these agents varied from 1 hour for glutaraldehyde to 5 days for glyceraldehydes to 30 minutes UVA irradiation for riboflavin/UVA. In this study, the riboflavin/UVA method, although rapid, may have also had the smallest effect in scleral stiffening because the poor penetration of UVA through scleral tissues. Blue light at 436 nm is also effective in crosslinking with riboflavin (Spoerl E, Seiler T. *J Refract Surg.*; 15(6):711-713 (1999)), and may be preferable due to its greater penetration in sclera. Additionally, as shown in Example 4, the use of a flash-linking compound achieves a similar therapeutic effect as riboflavin, but in a fraction of the UVA or blue light exposure time (Qian Y, et al. IOVS 2008: ARVO Abstract 3361).

Although glutaraldehyde is known to be cytotoxic, and riboflavin/UVA has been shown to cause retinal pigment epithelium (RPE), photoreceptor and outer nuclear layer death in rabbit eyes exposed to riboflavin and irradiated with 370 nm light at 4.2 mW/cm2, these crosslinking therapies can be regulated and dose adjusted to also reduce their penetration and consequent cytotoxic effect (Wollensak G, et al., *J Cataract Refract Surg.*; 30(3):689-695 (2004); Wollensak G, et al., *Acta Opthalmol Scand.*; 83(4):477-482 (2005)). Alternatively, a nonenzymatic glycation-induced crosslinking, with an agent like glyceraldehyde, can be implemented over a longer exposure period with good efficacy and without the potential loss of cell viability. In the previously cited study of porcine and human strips of peripapillary sclera (PS) and lamina cribrosa (LC) incubated in 0.5 M glyceraldehyde and 0.5 M methylglyoxal over a period of 5 days, the stress with 20% strain of human PS and LC revealed a >2 fold and >1.5 fold respective increase when exposed to glyceraldehydes and a >3 fold and >2 fold respective increase when exposed to methylglyoxal (Spoerl E, et al., *Invest Opthalmol Vis Sci.*; 46(4):1286-1290 (2005)). These two agents might be excellent choices if prolonged exposure could efficiently be delivered.

As discussed above, collagen based and connective tissue structures within (i.e., lamina cribrosa) and around the optic nerve (i.e., peripapillary sclera) provide structural support to the ganglion cell axons as they traverse the fenestrated meshwork of the lamina cribrosa within the optic nerve head. The lamina cribrosa (LC) itself is contiguous with and anchored to the peripapillary scleral (PS).

Since glaucomatous changes in response to elevated intraocular pressure may lead to expansion of the optic canal and peripapillary scleral wall, resulting in biomechanical strain on the lamina cribrosa, the initial elastic and later plastic deformation of these structures can be prevented and/or minimized by crosslinking of the annulus of scleral tissue surrounding the optic nerve at either its anterior or posterior extent. Since the anterior peripapillary sclera, in close proximity to the insertion of the lamina cribrosa, is covered by the retinal nerve fiber layer and peripapillary retina, access to this specific tissue can be more challenging and, in some instances, could require a highly focused application of activating energy such as UV light in combination with a non-toxic photosensitive crosslinking reagent. The anterior peripapillary sclera could also be approached with topical application of one of the agents described herein, particularly if the crosslinking effect is limited to collagenous structures deep to the nerve fiber layer and retina. The choroidal circulation could provide another selective route of delivery to the surrounding anterior peripapillary sclera if the crosslinking agent is able, through its native properties or with chemical modification, to exit the choroidal microvasculature through the many fenestrations present while remaining inside the non-fenestrated vessels that course within the retina. Posteriorly, crosslinking can be achieved by direct or endoscopic orbital visualization and drug delivery, as well as by fiber optic UVA light delivery.

Optic nerve sheath fenestration and decompression is a surgical procedure that is currently performed on an outpatient basis, and is achieveable with a medial or even lateral orbitotomy approach. This same technique for accessing the optic nerve sheath can be implemented for the peripapillary sclera. The medial orbitotomy technique is performed by disinserting the medial rectus muscle and rotating the globe laterally until the optic nerve comes into view of the surgical field. The orbital fat can be pushed away from the peripapillary sclera and optic nerve to access these structures for drug delivery. Alternatively, a small orbitotomy incision can be made followed by endoscopic visualization, then agent and light delivery.

Since the posterior aspect of the scleral canal is of larger diameter than the anterior aspect, application of riboflavin can be along the sclera, directly adjacent to and fully surrounding the optic nerve and its sheath. In one embodiment with riboflavin crosslinking, repeated applications every few minutes totaling ~30 minutes could be directed to the peripapillary sclera with or without the aid of iontophoresis, followed by UVA or blue light irradiation for a similar period of time. In iontophoresis, an electrical current is used to transport ionized agents through tissue, while imaging their depth and location of penetration (Wang Y, et al., *Ophthalmic Surg Lasers;* 27:484-487 (1996); Myles M E, et al, *Adv Drug Deliv Rev.;* 57: 2063-2079 (2005)). Directing the delivery of the crosslinking agent (with or without iontophoresis) and UVA light (~365-370 nm) or blue light (~465 nm) parallel to the optic nerve and obliquely inward toward the peripheral margin of the lamina cribrosa (see arrows in FIG. 1) can facilitate crosslinking along the posterior to anterior extent of the optic canal wall. The depth of penetration of crosslinking can be titrated based on the concentration of riboflavin (~0.05-0.2%), the depth of iontophoresis, the intensity of the UVA light (0.5-15 mW/cm$^2$) and the time of UVA exposure (5-60 minutes). Care must be taken to effect the proper degree of crosslinking while ensuring the safety of the underlying retinal structures, blood vessels and nerve fibers. A previous study of aggressive scleral crosslinking resulted in the desired stiffening, but with retinal damage (Wollensak, G, et al., *Acta Opthalmol Scand;* 83: 477-482 (2005)). A longer UVA wavelength (ranging from about 430 nm to about 475 nm) can be used with riboflavin to achieve the desired effectiveness while maximizing safety. Alternative photosensitizing agents could also be used, as above. For example, indocyanine green (ICG) promotes crosslinking and stiffening of collagen when photosensitized with visible light with a peak absorption at 700 nm and is already used routinely for imaging the choroidal and retinal circulation.

Aldehyde sugars and nitrite containing solutions (nitro alcohols (nitro alcohol based agent), nitrosamine, nitrites) can also be applied to the peripapillary sclera along the optic canal wall to effect crosslinking (Paik, D C., et al., 2007 ARVO abstract #4023). Glyceraldehyde, methylglyoxal or ribose are examples of aldehyde sugars and chemicals that can be targeted around the optic nerve in one or multiple applications. Since the time duration of exposure for crosslinking is typically longer than that required for riboflavin/UVA crosslinking, a sustained release depot or even iontophoresis of these agents might be placed around the optic nerve, allowing the agent to be more deeply penetrated or released over time. In a study of peripapillary scleral crosslinking with glyceraldehyde 0.5M and methylglyoxal 0.5 M, human scleral strips treated with these agents increased in stiffness by 2-3 times (Spoerl E, et al., *Invest Opthalmol Vis Sci;* 46:1286-1290 (2005)). Comparatively, scleral strips soaked in glyceraldehyde 0.2M for 5 days were more effective in crosslinking than riboflavin 0.1%/UVA for 30 minutes in both human and porcine eyes (Wollensak G, et al., *J Cataract Refract Surg;* 30:689-695 (2004)). Crosslinking with glutaraldehyde 0.1% (a chemical fixative agent), by soaking scleral strips for 1 hour, was the most effective crosslinker, but is also more toxic to ocular tissues (Wollensak G, et al., *J Cataract Refract Surg;* 30:689-695 (2004)).

As mentioned above, crosslinking of the lamina cribrosa might be more difficult because of the overlying nerve fiber layer anterior to this structure as well as below it. However, several agents may be used for crosslinking the lamina cribrosa without nerve damage, or under circumstances of advanced glaucoma, where the lamina cribrosa is directly apparent on opthalmoscopic exam.

Specific Crosslinking: Since riboflavin/UVA causes oxidative damage to adjacent cellular structures, its direct application with irradiation to the optic nerve head could be detrimental to the nerve fibers, except when the lamina cribrosa is exposed in advanced glaucoma. A monochromatic light source (i.e., UVA light at 465 nm) can be delivered in a transpupillarly fashion to specific posterior structures without significant absorption by the ocular media. Pinpoint delivery of light to the exposed lamina cribrosa can be facilitated with adaptive optics delivery. The delivery of light with adaptive optics has been previously described with dynamic visual stimulus presentation (microperimetry), where the resolution of light delivery is smaller than the size of single cone photoreceptors (Poonja S, et al., *J Refract Surg;* 21: S575-S580 (2005)). With intravenous injection of riboflavin, late staining of the optic disc with riboflavin can be achieved, as with fluorescein angiography, hence allowing adaptive optics localization of crosslinking to specific lamina cribrosa structures. Furthermore, early microvascular leakage of riboflavin from the choroidal vessels could be targeted with UVA to induce transpupillary crosslinking of the anterior peripapillary sclera.

Alternatively, direct application of indocyanin green (ICG), has been shown to increase the stiffness of the internal limiting membrane of the retina following exposure with white light for 3 minutes (Wollensak G, et al., *Opthalmologica;* 218: 278-282 (2004)). Intravenous injection of ICG, which is commonly accepted and used in retinal photodynamic therapy, would deliver this agent to the posterior segment, and lead to late staining of the optic disc, as with fluorescein. Visible light, delivered at its absorption peak of 700 nm or even white light, would crosslink the collagen structures stained with ICG, and with specific delivery of the light to the optic disc and lamina cribrosa, specific crosslinking would be observed. One might also anticipate that multiple injections of ICG together with chronic exposure to ambient white light might facilitate nonselective crosslinking of the lamina cribrosa, as well. As above, early leakage of this agent from the choroidal vasculature could be used to crosslink peripapillary sclera if sufficient penetration of the appropriate light wavelengths can be achieved.

Light Delivery System: In one embodiment, the light delivery device is the coupling of a scanning laser opthalmoscope or other fundus imaging device with a digitally illuminated circular disc or spot of uniform intensity (full or partial size of the exposed optic disc or LC) which could be directed by a projected aiming reticle and stabilizing optics for a defined exposure period. Alternatively, a small pinpoint of light or small spot defined by adaptive optics imaging and delivery (Poonja S, et al., *J Refract Surg;* 21: S575-S580 (2005)) can be targeted onto specific portions of the LC, so as to specifically target the collagen meshwork and avoid the vital optic nerve structures that are adversely effected by the light. Also, intravitreal delivery of the light and/or photosensitizing substance could be performed by a fiber optic and/or micropipette system.

Thermal Delivery System: Transpupillary thermotherapy is an established technique of delivering focusable thermal energy to the choroid for the purpose of destroying neoplasms without extensive destruction of surrounding tissue. A similar technique using thermal or convergent ultrasound energy could be used to deliver focused heat to the peripapillary sclera deep to the choroid. Thermal energy is proven mechanism of collagen crosslink induction and could also contribute to peripapillary stiffening by causing fibrosis.

Nonspecific Crosslinking: Nonenzymatic crosslinking (glycation) of proteins and collagen stiffens these soft tissues over a period of many years, as in the example of diabetes (Girton T S, et al., *J Biomed Mater Res;* 60: 384-391 (2002)). As used herein, "nonenzymatic glycation" refers to a reaction in which reducing sugars are covalently bound to free aminogroups of macromolecules. Just as delivery of a topical aldehyde sugars, or other agents such as nitrosamine and nitrites, induces crosslinking of the cornea and other ocular structures, intravitreal delivery of these agents with multiple injections or an insert could facilitate collagen and protein stiffening inside the eye over a period of weeks to months (Girton T S, et al., *J Biomed Mater Res;* 60: 384-391 (2002)). Just simply using these as topical agents might facilitate stiffening of posterior structures, but only after a period of years to decades. Alternate forms of delivery to both the lamina cribrosa and peripapillary sclera, include intravenous, intravitreal, subtenons, retrobulbar and intrathecal. In one embodiment, a sustained release reservoir of these agents would be placed on top of the peripapillary sclera surrounding the optic nerve, and slowly release the agent over a period of weeks, months or years. In some instances, nonenzymatic crosslinking, as with aging and diabetes, could have deleterious effects (Avery N C, Bailey A J., *Pathologie Biologie;* 54: 387-395 (2006)). Additional mediation of the Maillard reaction (nonenzymatic crosslinking) can be advanced with agents such as 3-deoxyglucosone or even inhibited with other agents such as aminoguanidine (Igaki N, et al., *Clin Chem;* 36: 631-634 (1990)). Aminoguanidine, in addition to being an inhibitor of nonenzymatic crosslinking, has also been demonstrated to have a neuroprotective effect to retinal ganglion cells by inhibiting nitric oxide synthase (Neufeld A H., *Brain Res Bull;* 62:455-459 (2004)). Other crosslinking enhancing agents, such as 3-deoxyglucosone and methylglyoxal have demonstrated a neurotoxic effect to cortical neurons, so that use of these agents in crosslinking the lamina cribrosa or even peripapillary sclera need to avoid direct exposure to the optic nerve fibers or retinal cells (Kikuchi S, et al., *J Neurosci Res;* 57:280-289 (1999)). Cotreatment with aminoguanidine and pretreatment with N-acetylcysteine, however, protected the neurons from the neurotoxic effect of these agents, which suggests that coincident exposure might be possible (Kikuchi S, et al., *J Neurosci Res;* 57:280-289 (1999)).

Scleral Compliance: Given evidence that the lamina cribrosa bows posteriorly in response to raised IOP and in the setting of glaucoma, a hypercompliant lamina cribrosa may not stiffen as readily as the surrounding sclera when crosslinking is attempted. An alternative to reinforcing the lamina cribrosa's resistance to strain might involve decreasing the stiffness of the sclera some distance away from the optic nerve to redirect the burden of pressure away from the lamina cribrosa for absorption by a more compliant region of the sclera. This increase in scleral compliance can be achieved with pharmacologic means, such as collagenases, matrix metalloproteinases or hyaluronidase, or mechanical means, such as focal surgical thinning or fenestration of an area of sclera with laser, thermal or incisional techniques. The above scenario would highlight the idea of differential crosslinking whereby different regions of the sclera are made stiffer, while other regions (such as the supraciliary sclera) could be made more flexible. The optimum distribution of these differences (whether differences in depth or extent of crosslinking or cross-link inhibition) could be investigated and tested with computational models.

In particular embodiments, the agent for use in the methods is riboflavin in combination with light such as UV light and/or blue light. The riboflavin concentration can range from about 0.05% to about 0.2% and the wavelength of the light can range from about 365 nm (UVA) to about 430 nm-about 475 nm (blue light). The riboflavin can be applied, for example, topically. The time needed to exposure the collagen of the PS and/or LC will vary depending upon a number of factors (e.g., the light used; the condition being treated). In one embodiment, exposure of the light ranges from about 1 minute to about 60 minutes. In other embodiments, the agent for use in the methods is glutaraldehyde. In still other embodiments, the agent is methylglyoxal and/or glyceraldehyde.

As described herein, the agent causes crosslinking of the collagen of the peripapillary sclera and/or lamina cribrosa. In one embodiment, stiffness of the peripapillary sclera increases from about 1.2-fold to about 50-fold after contact with the agent. In a particular embodiment, the stiffness of the peripapillary sclera increases about 20-fold after contact with the agent.

As described herein, the methods of the invention are used to protect (e.g., inhibit loss of) all or a portion of the optic nerve fiber layer within the optic nerve/lamina cribrosa complex, treat glaucoma and/or treat glaucomatous optic neuropathy in an individual in need thereof. The methods can be performed in an individual who does not have glaucoma or glaucomatous optic neuropathy (e.g., prior to the onset of glaucoma or glaucomatous optic neuropathy; in individual at risk of developing glaucoma or glaucomatous optic neuropathy), has early stage glaucoma or glaucomatous optic neuropathy or advanced (late-stage) glaucoma or glaucomatous optic neuropathy. In one embodiment, one or more of the methods described could be performed early in the course of glaucoma in an individual, when optic canal wall has not been significantly expanded (e.g., prior to significant scleral canal wall expansion and/or posterior deformation of the lamina cribrosa) or later following a significant level of expansion of the peripapillary sclera, and stretching of the lamina cribrosa. Early crosslinking might prevent or minimize the strain placed onto the lamina cribrosa by elevated intraocular pressure, while late crosslinking might reduce the indirect stress on the lamina cribrosa due to elevated IOP.

Furthermore, the methods can be performed on an individual who has low IOP (<12 mmHg), normal (physiologic) intraocular pressure (12-21 mmHg), or high intraocular pressure (>21 mmHg).

As used herein, "treating" means preventing the onset, slowing the progression of and/or reversing some or all of the conditions or symptoms of glaucoma or glaucomatous optic neuropathy in an individual. In particular embodiments, the individual is a mammal (e.g., primate (e.g., human), canine, feline and the like).

The (one or more) agent is administered in an "effective amount" or in a "therapeutically effective amount" (i.e., an amount that is sufficient to treat the condition or disease, such as by ameliorating symptoms associated with the condition or disease, preventing or delaying the onset of the condition or disease, and/or also lessening the severity or frequency of symptoms of the condition or disease). The amount that will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

The one or more agents can be delivered in a composition, as described above, or by themselves. They can be administered systemically, or can be targeted to a particular tissue. The agent can be produced by a variety of means, including chemical synthesis.

In a particular embodiment, the agent is a pharmaceutical agent. The agent for use in the methods described herein can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The methods described herein provide a therapy for an existing, common eye disease (e.g., glaucoma). The methods treat the underlying problem of biomechanical vulnerability of the lamina cribrosa and peripapillary sclera (which creates excessive strain due to the stress of high intraocular pressure), rather than trying to reduce the stress of high IOP alone. Agents for use in the methods can be delivered behind the eye (intraorbitally) onto the scleral tissue surrounding the optic nerve or inside the eye (intraocularly) onto the exposed collagen of the lamina cribrosa within the optic cup by one of several advanced imaging and light delivery techniques and/or by a novel method of delivery of the crosslinking agent. Intraorbital exposure of the light and crosslinking agent to the peripapillary sclera can be performed by extraocular muscle disinsertion and eye globe rotation to expose the target tissue or by endoscopic fiber optic light delivery and drug delivery. Intraocular exposure of the light and crosslinking agent to the collagen of the lamina cribrosa (LC) can be performed by transpupillary focusing of 436-465 nm UVA light (or 700 nm light or thermal or convergent ultrasound energy) with or without the aid of adaptive optics to specific exposed regions of the LC or peripapillary sclera after it has been photosensitized with riboflavin (or indocyanine green) delivered by one of several methods (intravenously, intravitreally, intrathecally, etc). The viscoelastic collagen abnormality and biomechanical vulnerability of the lamina cribrosa and peripapillary sclera in glaucoma parallels the corneal and scleral abnormalities which have already been demonstrated in keratoconus and pathologic myopia, respectively. The crosslinking concepts presented in the treatment of glaucoma parallels the treatment methods which are currently being used clinically in keratoconus.

In addition, the methods described herein can be used with a variety of other methods used to treat conditions such as high IOP and/or glaucoma. For example, the methods described herein can be used in combination with (1) Priavision Sonic Eye (device measuring elastometry by the surface wave velocity between two points; (2) Priavision Keracure (headset device for delivering 365 nm UVA light at 3.0 W/cm$^2$ at the corneal plane; (3) Riboflavin 0.1%; (4) Adaptive optics scanning laser opthalmoscope; (5) Methods for optical coherence elastography of the eye (Dupps et al, *J. Refract. Surg.* 23:66-75 (2007)), for studying the effect of candidate crosslinking interventions on the structures of interest in vivo, and for determining risk of glaucoma progression and suitability for the proposed treatment.

Although the clinical delivery of crosslinking agents for the stiffening of the peripapillary sclera might be considered difficult due to the posterior anatomy of the peripapillary sclera, several possible techniques might be implemented to improve upon its accessibility. Firstly, medial rectus disinsertion with globe rotation might be considered, as performed during optic nerve sheath decompression surgery (Hupp S L, et al., *Arch Opthalmol.;* 105(3):386-389 (1987)). Alternatively, access using a specialized endoscopic probe for drug and fiber optic light delivery and visualization could be considered. With previous reports of both flexible and rigid orbital endoscopy and surgery (Braunstein R E, et al., *Ophthal Plast Reconstr Surg.,* 11(4):269-272 91995); Prabhakaran V C, Selva D. *Indian J Opthalmol;* 56(1):5-8 (2008)), similar to endoscopic sinus surgery, this intervention could be a realistic approach and ultimately less invasive than complex filtering or shunting procedures. Whatever the best method, protecting the laminar region of the optic nerve from injurious deformation by modifying surrounding scleral properties represents a conceptual shift in the management of glaucoma that could complement conventional IOP-lowering therapies by reducing the risk of neuronal injury at any given IOP level.

The work described herein explores the mechanical effects upon the ON/LC of modifying peripapillary scleral stiffness, and has several limitations. The effect of PS crosslinking on PS and ON/LC deformation was assessed with a simple optical approach that only considered radial deformation. Posterior deformation of the LC is an important morphologic feature of glaucoma that may contribute to axonal injury (Bellezza A J, et al., *Invest Opthalmol Vis Sci.;* 44(2):623-637 (2003); Yang H, et al., *Invest Opthalmol Vis Sci.;* 48(10): 4597-4607 (2007); Downs J C, et al., *Invest Opthalmol Vis Sci.;* 48(7):3195-3208 (2007)), and our study was not designed to measure potential consequences of peripapillary stiffening on posterior laminar strain. The insulating effect of PS crosslinking on both laminar stiffness and strain were observed over a non-physiologically high pressure increment in porcine tissue and needs to be explored in human tissue over a range of pressure increments more likely to be encountered in the setting of primary open angle glaucoma. Further work in this area will likely include the demonstration of any efficacy in prevention or treatment of "clinical" glaucoma, which require additional work in living animal models, and the safety testing of various peripapillary crosslinking approaches and their secondary effects on neuronal and vascular function have yet to be explored in vivo (Spoerl, E., et al., *Invest. Opthalmol. Vis. Sci.,* 46(4):1286-1290 (2005)).

EXAMPLE 1

The Effects of Intraocular Pressure Elevation on Papillary Stiffness Before and after Riboflavin/Ultraviolet-A Induced Collagen Crosslinking Purpose To evaluate the biomechanical effect of riboflavin-UVA crosslinking of the lamina cribosa and peripapillary sclera of the porcine optic nerve.

Methods

Surface wave velocity (SWV) is a measure of tissue stiffness, and is performed by detecting the velocity of an ultrasonic wave between 2 points (Sonic Eye, Priavision, Menlo Park, Calif.) (Dupps W J, et al., *J Refract Surg;* 23: 66-75 (2007)). 19 porcine eyes were divided into 2 groups. In group 1 (6 eyes), the SWV across the exposed optic nerve/lamina cribrosa complex (ON/LCC) was initially measured at the eyes' physiologic IOP and at 100 mmHg. The porcine globes were cannulated with IV tubing to facilitate the change in IOP. In group 2 (13 eyes), the pre-treatment SWV was measured across the same region and atop the peri-papillary sclera, after which both regions were treated with riboflavin 1%, Q 5 min×6, and UVA irradiation (~365 nm at 3 mW/cm$^2$ for 30 min per eye. The SWV was then re-measured in each eye at the pre-treatment IOP and at 100 mmHg.

Results

In group 1, the SWV of the ON/LCC was 27.5±1.0 m/s (mean±SD) at physiologic IOP and increased to 36.6±0.9 mm/s at 100 mmHg (p=0.04). In group 2, crosslinking increased the stiffness of the ON/LCC from 26.0±1.2 to 32.8±1.1 m/s (p<0.001), while the peripapillary sclera increased from 29.7±1.2 to 55.7±1.5 m/s (p<0.001). Upon rising the IOP to 100 mmHg, the SWV of the ON/LCC showed no change (p=0.1), while it increased further along the peripapillary sclera to 63.5±1.8 m/s (p=0.007).

Conclusions

IOP elevation and riboflavin/UVA crosslinking independently increased the stiffness of the ON/LCC, and the latter increased the stiffness of the peripapillary sclera. However, after crosslinking, the pressure elevation caused increase stiffness in the peripapillary sclera, but not in the ON/LCC. Based on these findings, it is likely that the increased stiffness of the crosslinked peripapillary scleral ring limits the impact of increasing IOP along the crosslinked lamina cribosa. This likely has indications in the pathophysiology and treatment of glaucomatous optic neuropathy.

EXAMPLE 2

Glutaraldehyde Crosslinking of Peripapillary Sclera

The study described in Example 1 was expanded upon by repeating these experiments in 6 porcine eyes, using glutaraldehyde (GTA) as a more potent crosslinking agent. An annular sponge soaked in GTA was exposed to the peripapillary sclera for ~30 minutes, and not the ON/LCC. Measurements were repeated as above, but also along each quadrant of peripapillary sclera to ensure uniformity and symmetry of crosslinking around the ON/LCC. The results are summarized as follows:

| Mean IOP | Mean ON/LCC Stiffness | Mean PPS Stiffness |
|---|---|---|
| Before Glutaraldehyde Crosslinking | | |
| 2.3 mmHg | 25.7 m/s | 27.9 m/s |
| 80 mmHg | 29.5 m/s | 64.8 m/s |
| After Glutaraldehyde Crosslinking | | |
| 3 mmHg | 29.5 m/s | 83.6 m/s |
| 80 mmHg | 29.3 m/s | 97.9 m/s |

The following points was concluded from the data:

1) The surface wave velocity can be reproducibly measured in ex-vivo tissue structures, and that it reflects the rigidity/elasticity (Stiffness) of these structures.

2) ON/LCC and PS stiffness is nearly identical at low IOP.

3) When raising the IOP from low to high, the stiffness of the PS more than doubles (p<0.0001), while the ON/LCC stiffness increases by ~15% (p<0.0001).

4) When crosslinking only the PS, the stiffness of the PS increases under both low pressure (p<0.0001) and high pressure conditions (p<0.0001), suggesting a real change in the tissue properties.

5) When crosslinking only the PS, the stiffness of the ON/LCC increases only slightly under low pressure conditions (p<0.0001), but also remains the same as the IOP increases to higher levels (p=0.77).

6) These findings indicate that the peripapillary scleral ring protects the ON/LCC from the circumferential tension brought about by high IOP, and also that the stress of high IOP has more of an impact on circumferential tension than it does upon direct compression of the ON/LCC.

7) These findings indicate further that crosslinking of the peripapillary scleral ring continues to protect the ON/LCC from the stress of high IOP, even while its stress/strain ratio increases.

8) These conclusions are supported by the macroscale and microscale biomechanical modeling of the lamina cribrosa and scleral ocular coat, whereby both a thickening and stiffening of the peripapillary sclera lowers the laminar stress and strain (Sander E A, et al., *J Biomechan Eng;* 128:879-889 (2006)).

EXAMPLE 3

Biomechanical Effects of Intraocular Pressure Elevation on Optic Nerve/Lamina Cribrosa before and after Peripapillary Scleral Collagen Crosslinking Purpose To evaluate the biomechanical effect of intraocular pressure (TOP) elevation on the optic nerve/lamina cribrosa complex (ON/LC) and peripapillary sclera (PS) of porcine eyes before and after localized collagen crosslinking.

Methods

Eighteen porcine globes were divided evenly into 3 groups. The optic nerves were transected to expose the ON/LC, and each globe was infused through an in-line pressure transducer for direct IOP control. Surface wave velocity, a non-destructive measure of tissue stiffness, was measured across the ON/LC and PS before and after collagen crosslinking at IOP of 10 and 30 mmHg (groups 1 and 2) and at each globe's preinflation IOP and 80 mmHg (group 3). In group 3, papillary strain was measured by analyzing the displacement of fiducial marks immediately adjacent to the ON/LC using digital photography. Crosslinking in group 1 was achieved with riboflavin-ultraviolet A (UVA) delivery to the entire ON/LC and PS and, in groups 2 and 3, with an annular sponge soaked in glutaraldehyde (GTA) and applied only to the PS.

Results

Native PS was significantly stiffer than the ON/LC across all experiments. Before crosslinking, IOP elevation caused significant stiffening of both the ON/LC and PS. After crosslinking with either technique, IOP elevation stiffened the PS but not the ON/LC region. In group 3, papillary strain during IOP elevation was significantly reduced after PS crosslinking.

Conclusion

Stiffening of the peripapillary scleral ring reduces the biomechanical sensitivity of the optic nerve/lamina cribrosa complex to IOP elevation and may represent a novel mechanism for neuroprotection in glaucoma.

Methods

Surface wave velocity (SWV) is a measure of tissue stiffness that has been used in dermatologic applications to measure age-related changes (Potts R O, et al., *J Invest Dermatol.;* 82(1):97-100 (1984); Potts R O, et al., *J Biomech.;* 16(6):365-372 (1983); Davis B R, et al., *Exp Gerontol;* 24(3):201-210 (1989)), softening effects of tissue hydration and skin creams (Vexler A, et al., *J Invest Dermatol;* 113(5):732-739 (1999)), and sclerosing effects of radiation on breast skin (Gorodetsky R, et al., *Int J Radiat Oncol Biol Phys.;* 45(4):893-900 (1999)). When acoustic waves in the 0.5 to 30 kHz frequency range are used, propagation speed in skin is related to the density and stiffness of the tissue (Pereira J M, et al., *J Biomech.;* 23(8):745-751 (1990)). A prototype handheld ocular surface elastometer (Sonic Eye, Priavision, Menlo Park, Calif.) with an operating frequency within this range (4 kHz) and a fixed 4.5 mm wave propagation distance has been described in detail elsewhere (Dupps W J Jr, et al., *J Refract Surg.;* 23(1):66-75 (2007)). The Sonic Eye was used in this study as a non-destructive means of measuring local in situ tissue stiffness across and around the optic nerve head.

Figures 3A, 3B:
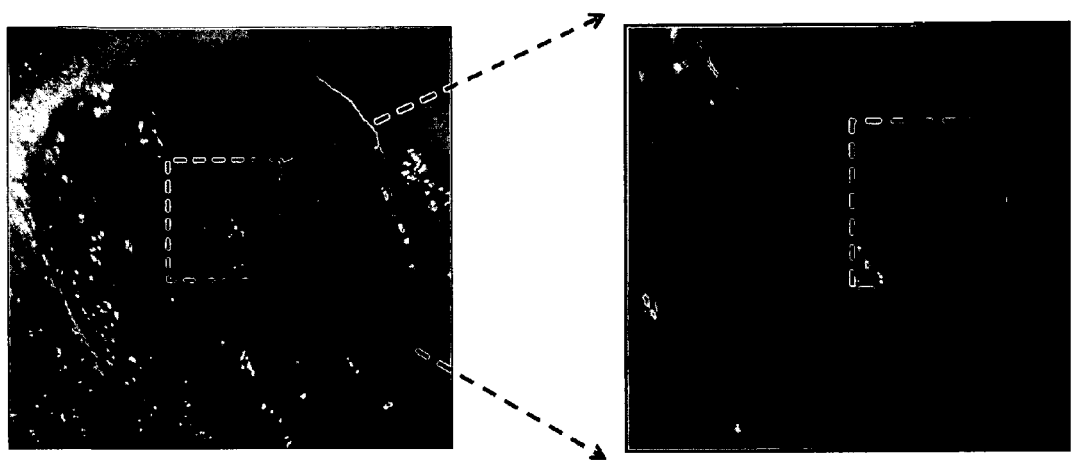
FIG. 3a (left) shows an experimentally exposed Optic Nerve/Lamina Cribrosa Complex after transecting the Optic Nerve with a Surgical Blade.
FIG. 3b (right) shows magnification of FIG. 3a, and thus shows exposed Lamina Cribrosa.
Figure 4:
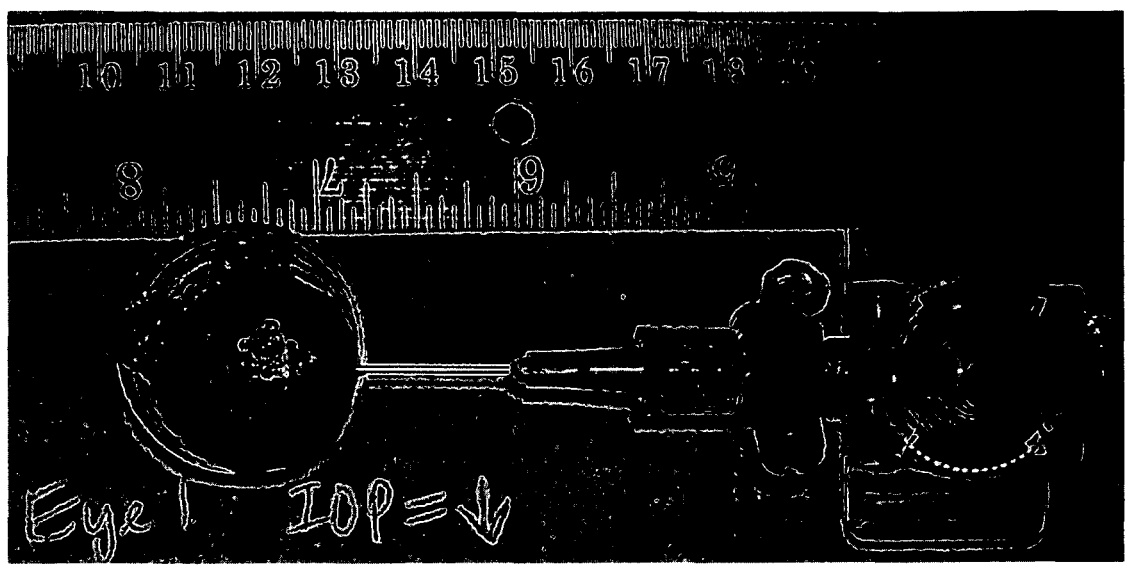
FIG. 4 shows an In-Line Pressure Transducer Infused with Normal Saline for Direct Intraocular Pressure Control.
Figure 5:
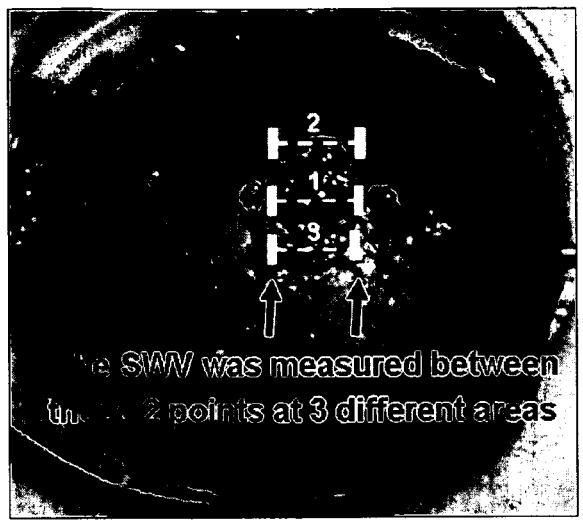
FIG. 5 shows Surface Wave Velocity measurements were taken between 2 points using the Sonic Eye Elastometer atop the Optic Nerve/Lamina Cribrosa Complex (area 1) and the Peripapillary Sclera (area 2 & 3). Note the fiducial marks placed immediately adjacent to the Optic Nerve/Laminal Cribrosa Complex in group 3 eyes.

Eighteen porcine eyes were obtained from a local abattoir (Heffelfingers Meats, Inc., Jeromesville, Ohio) and were used within 24 hours postmortem. The optic nerves were dissected under microscopic visualization to expose the ON/LC (FIG. 1). As shown in FIG. 2, vitreous infusion of normal saline through a 23-gauge needle (BD, Franklin Lakes, N.J.) and in-line pressure transducer (Biotrans 2, Biosensors International, Inc., Singapore) provided direct IOP control and measurement capabilities (Infinity SC9000XL digital pressure monitor, Drager Medical, Lubeck, Germany). Three SWV measurement positions were defined as illustrated in FIG. 3 to provide comparable papillary (ON/LC) and circumferentially oriented peripapillary stiffness measurements across experiments. Replicate SWV measurements were obtained at a rate of 1 per second with a triggering foot pedal to produce at least 5 measurements that were subsequently averaged for each region of interest. A PC software interface converted the time-of-flight data to velocity in meters per second (m/s), and the velocity data were exported to Excel (v. 11, SP2; Microsoft Corp, Redmond, Wash.) and Minitab (v. 14.20; Minitab Inc, State College, Pa.) for statistical analysis.

Three experimental groups of 6 eyes each were defined. In group 1, SWV across the optic nerve/lamina cribrosa complex and peripapillary scleral regions of interest were measured at 10 and 30 mmHg to represent a physiological range of pressures. Next, both the ON/LC and PS regions were treated with topical riboflavin 1% every 5 minutes during 30 minutes of continuous UVA irradiation (Wollensak G, et al., *Am J Opthalmol.;* 135(5):620-627 (2003)) using a light source at a wavelength of 365 nm and energy of 3 mW/cm2 (PriaVision, Menlo Park, Calif.). SWV was then re-measured at each region of interest at 10 and 30 mmHg. Three peripapillary sclera measurements were obtained along two quadrants immediately adjacent to the ON/LC (FIG. 3) and averaged to arrive at a mean circumferential stiffness.

In group 2 (n=6), a protocol similar to that described in group 1 was repeated at 10 and 30 mmHg. However, instead of applying riboflavin/UVA irradiation, an annular sponge (inner diameter 3.5 mm, outer diameter 8 mm) soaked in 4% GTA diluted from 8% electron microscopy grade stock (Polysciences, Warrington, Pa.) was positioned over the PS for 30 minutes with deliberate avoidance of the ON/LC. Measurements were then repeated at both IOP levels.

In group 3 (n=6), the same procedure described for group 2 was implemented with the following exceptions. First, four fiducial ink marks were placed in each quadrant of the PS immediately adjacent to the ON/LC prior to measurement. High-resolution (7.1 megapixel) digital photos were then taken at both low and high IOP before and after crosslinking. The vertical and horizontal distances between the outer extent of the ink marks and the outer margins of the optic nerve were measured in Photoshop (Adobe Systems, Inc., San Jose, Calif.), and the centripetal displacement of the fiducial marks ($\Delta 1$) was divided by the initial distance between the marks (10) to yield dimensionless indicators of circumferential strain ($\zeta = \Delta 1/10$) in the peripapillary sclera and ON/LC, respectively. Second, measurements were acquired at each eye's pre-inflation pressure (between 2 to 4 mmHg) and at 80 mmHg to ensure that measurable changes in SWV and ON/LC geometry would be generated in at least one experimental group. As in group 2, the peripapillary sclera was selectively exposed to GTA and post-crosslinking measurements were repeated at low and high IOP. Same-eye statistical comparisons of wave velocity and strain were performed with paired student's t-tests.

Results

Table 1 summarizes surface wave velocity measurements in each group at low and high IOP before and after collagen crosslinking. Across all groups, native peripapillary scleral stiffness exceeded that of the optic nerve/lamina cribrosa complex by at least a factor of 2 at low IOP (59.2±4.6 m/s for PS vs. 27.9±2.4 m/s for ON/LC, p<0.001) and more at high IOP (125.7±21.5 m/s for PS vs. 27.5±3.2 m/s for ON/LC, p<0.001). In Group 1, riboflavin/UVA exposure of the entire papillary and peripapillary region had no measurable effect on the stiffness of the ON/LC (p=0.57), but significantly increased the PS stiffness from 58.9±2.3 to 121.1±17 m/s (p=0.004) at 10 mmHg. No significant crosslinking-induced changes in stiffness were observed at an IOP of 30 mmHg in the ON/LC (p=0.33) or PS (p=0.35). Only the PS stiffened significantly with an increase in IOP before (p<0.001) and after crosslinking (p=0.002).

In Group 2, only an annulus of peripapillary sclera was exposed to GTA. Focused PS crosslinking had no significant impact on ON/LC stiffness at measurement pressures of 10 mmHg (p=0.56) and 30 mmHg (p=0.9). GTA-mediated increases in peripapillary scleral stiffness, however, were significant at 10 mmHg (from 64.0±1.8 to 148.4±43.0 m/s, p=0.005) and marginally significant at 30 mmHg (141.9±20.5 to 197.0±35.6 m/s, p=0.05). In addition, as IOP was increased, ON/LC stiffness actually decreased slightly when crosslinked (p=0.038), an effect that was not present prior to crosslinking (p=0.23). As in group 1, IOP increases caused significant PS stiffening both before (p<0.001) and after crosslinking (p=0.017, Table 1).

Group 3, like Group 2, involved focal GTA-mediated crosslinking of the PS region, but incorporated a much larger IOP range. Under pre-inflation IOP conditions (2-4 mmHg), ON/LC stiffness increased significantly from 25.7±1.6 to 29.5±2.9 m/s with peripapillary scleral crosslinking (p=0.003), a phenomenon that may relate to the nonlinearity of ocular compliance over this extended range of loads. Similar to the results in the other groups at a maximum IOP of 30 mmHg, localized PS crosslinking had no effect on ON/LC stiffness at a fixed IOP of 80 mmHg (p=0.91). PS stiffness was significantly increased by crosslinking when compared at fixed pre-inflation pressures (54.8±3.6 to 149.9±35.7 m/s, p<0.001) and at 80 mmHg (114.0±19.0 to 190.2±45.8 m/s, p=0.003). The peripapillary sclera stiffened with increasing IOP both before (p<0.001) and after annular PS crosslinking (p=0.029). However, regarding the laminar impact of increased IOP, the ON/LC stiffened significantly with IOP loading prior to PS crosslinking (p=0.003) but not after (p=0.87).

Finally, in Group 3, a photographic strain analysis during IOP elevation (Table 2) revealed significant centripetal peripapillary scleral strain both horizontally (6.5±4.2%) and vertically (8.1±4.9%) when measured prior to annular crosslinking. By a similar analysis of strain across the ON in the same eyes, the pressure-induced change in ON diameter was 10.5±3.9% horizontally and 9.4±6.5% vertically prior to crosslinking. The combined vertical and horizontal strain averaged 7.3±4.4% across the PS ring and 10.2±5.4% across the ON/LC region alone (p=0.22). After annular crosslinking, PS ring strain and ON/LC strain during IOP elevation were both significantly lower (p≤0.012 in all comparisons) and nearly immeasurable in both the horizontal and vertical directions (Table 2). The secant modulus (E) across the PS ring was then estimated both before and after crosslinking by deriving the circumferential stress increment according to thin-walled pressure vessel theory using the LaPlace equation (Fung Y C. Biomechanics: Mechanical Properties of Living Tissues. 2nd ed. New York, N.Y.: Springer-Verlag; 1993) and dividing by experimental strains from Group 3 (see Appendix). Resulting estimates of the PS ring elastic modulus were 836 kPa prior to crosslinking and 16.1 MPa after crosslinking. The native stiffness value compares favorably to the porcine scleral modulus of 500 kPa measured by Pierscionek B K, et al., *Br J Opthalmol.*; 91(6):801-803 (2007) particularly since their measurement was obtained at a lower peak pressure (50 mmHg) and was obtained from the entire sclera, which incorporates the thinner and effectively more elastic sclera anterior to the posterior pole (Olsen T W, et al., *Invest Opthalmol Vis Sci;* 43(8):2529-2532 (2002)).

Conclusions

IOP elevation measurably increases the in situ stiffness of the ON/LC and PS and is accompanied by circumferential strain in both regions. Collagen crosslinking of the PS measurably stiffens the PS and buffers the ON/LC from stiffening and circumferential strain during IOP elevation. These observations may have implications for modifying stress and strain-based mechanisms of injury in glaucomatous optic neuropathy.

Appendix

The elastic modulus (E) of peripapillary sclera (PS) in Group 3 was estimated before and after crosslinking. First, measured PS strain was divided into the circumferential stress as derived from the LaPlace equation, $$\sigma = IOP \times R/2t,$$

where $\sigma$ indicates the circumferential stress as a function of IOP, scleral radius of curvature (R), and sclera thickness (t). R and t for the posterior sclera of a typical medium porcine globe have been reported as 9.4 mm (Pierscionek B K, et al., *Br J Opthalmol.;* 91(6):801-803 (2007)) and 0.78 mm (Olsen T W, et al., *Invest Opthalmol Vis Sci.;* 43(8):2529-2532 (2002)), respectively. This radius was derived from a fit of one sagital profile of the whole globe to a best-fit sphere at 15 mmHg and was reported to increase 0.1 mm/mmHg TOP increase up to 50 mmHg (Pierscionek B K, et al., *Br J Opthalmol.;* 91(6):801-803 (2007)). Because specific knowledge of local curvature changes at the posterior pole is lacking, we assumed a constant local radius of curvature for the peripapillary sclera. Given that 1 mmHg is equivalent to 0.1333 kPa, over the increment from 4 to 80 mmHg, circumferential stress, $\sigma$, increased from a value of 3.21 kPa (or 4 mmHg*0.1333 kPa/mmHg*[9.4 mm/(2*0.78 mm]) to a value of 64.3 kPa (or 80 mmHg*0.1333 kPa/mmHg*[9.4 mm/(2*0.78 mm)]. Next, the circumferential stress increment (64.3-3.2 kPa) was divided by the resulting strain values for uncrosslinked (7.3%) and crosslinked (0.38%) PS to yield Epre-crosslinking=836 kPa and Epost-crosslinking=16.1 MPa.

TABLE 1

Stiffness (m/s) of the Optic Nerve/Lamina Cribrosa Complex and Peripapillary Sclera before and after Crosslinking at Low and High Intraocular Pressures

| | | Optic Nerve/Lamina Cribrosa Complex | | | Peripapillary Sclera | | |
|---|---|---|---|---|---|---|---|
| | | Pre-crosslinking Mean ± SD | Post-crosslinking Mean ± SD | p-value | Pre-crosslinking Mean ± SD | Post-crosslinking Mean ± SD | p-value |
| Group 1 | Low IOP | 28.1 ± 1.8 | 28.0 ± 1.6 | 0.57 | 58.9 ± 2.3 | 85.5 ± 13.5 | 0.004 |
| | High IOP | 25.7 ± 4.0 | 27.1 ± 1.8 | 0.33 | 121.1 ± 17.0 | 132.7 ± 20.2 | 0.35 |
| | p-value | 0.23 | 0.39 | | <0.001 | 0.002 | |
| Group 2 | Low IOP | 29.9 ± 1.8 | 29.1 ± 2.5 | 0.56 | 64.0 ± 1.8 | 148.4 ± 43.0 | 0.005 |
| | High IOP | 27.3 ± 2.4 | 27.4 ± 2.4 | 0.9 | 141.9 ± 20.5 | 197.0 ± 35.6 | 0.05 |
| | p-value | 0.23 | 0.038 | | <0.001 | 0.017 | |
| Group 3 | Low IOP | 25.7 ± 1.6 | 29.5 ± 2.9 | 0.003 | 54.8 ± 3.6 | 149.9 ± 35.7 | <0.001 |
| | High IOP | 29.4 ± 2.1 | 29.3 ± 1.9 | 0.91 | 114.0 ± 19.0 | 190.2 ± 45.8 | 0.003 |
| | p-value | 0.003 | 0.87 | | <0.001 | 0.029 | |

SD = standard deviation;
IOP = intraocular pressure;
All = combined data of Group 1, 2, and 3;
bolded values = p-values < 0.05;
*multivariable analysis

TABLE 2

Horizontal and Vertical Circumferential Strain (%) of the Optic Nerve/Lamina Cribrosa Complex and Peripapillary Sclera with Intraocular Pressure Elevation before and after Crosslinking

| | Strain (%) | Pre-Crosslinking Mean ± SD | Post-Crosslinking Mean ± SD | p-value |
|---|---|---|---|---|
| ON/LC | Horizontal | 10.5 ± 3.9 | 0.0 ± 0.0 | 0.002 |
| | Vertical | 9.4 ± 6.5 | 0.0 ± 0.0 | 0.012 |
| | Average | 10.2 ± 4.9 | 0.0 ± 0.0 | |
| PS | Horizontal | 6.4 ± 4.2 | 0.0 ± 0.0 | 0.01 |
| | Vertical | 8.1 ± 4.9 | 0.7 ± 1.9 | 0.011 |
| | Average | 7.3 ± 4.4 | 0.4 ± 1.3 | |

ON/LC = optic nerve/lamina cribrosa;
PS = peripapillary sclera;
SD = standard deviation;
bolded values = p-values <0.05

EXAMPLE 4

Comparative Study of UVA Riboflavin Crosslinking and "Flash-Linking" Using Surface Wave Elastometry Purpose To investigate comparative cornea stiffness values in porcine corneas after standard crosslinking and a new, rapid method of crosslinking (flash-linking) using surface wave elastometry (Sonic Eye, PriaVision Inc, Menlo Park, Calif.).

Methods

Six porcine eyes were treated using a UVA double diode with 4.2 mW/cm2 UVA at 370 nm while applying 0.1% riboflavin-5-phosphate drops to the central cornea every 5 minutes as a photosensitizer for 30 min (group 1). The next 6 porcine corneas were treated with a single application of a customized photoactive crosslinking agent (PriaVision Inc) and 30 seconds of UVA light at the same power and wavelength (group 2). Following both experimental treatments, the Sonic Eye system was used to measure ultrasound surface wave propagation time between two fixed-distance transducers applied to the cornea along central horizontal and vertical positions. Intraocular pressure was continuously monitored using a digital pressure monitor display (Infinity SC9000XL, Drager medical, Lubeck, Germany) after vitreous chamber cannulation with a 23-gauge needle.

Results

Mean surface wave velocity was 93.63±2.58 m/s in group 1 vs. 82.78±2.58 m/s in group 2 before treatment and 111.35±2.16 m/s (group 1) vs. 108.48±2.42 m/s (group 2) after crosslinking. The mean surface wave velocity increased by 17.7 units from 93.6 to 111.3 m/s (p=0.032) after crosslinking with UVA+riboflavin, and by 25.62 m/s from 82.78 to 108.48 m/s (p=0.002) after "flash-linking" with the customized photoactive crosslinking agent. No statistically significant differences in surface wave velocity were noted after crosslinking between group 1 and group 2 (p=0.75).

Conclusion

A new, rapid method of crosslinking (flash-linking) is introduced by the use of a customized photoactive crosslinking agent. The method demonstrates similar efficacy in stiffening the cornea (when measured with surface wave elastometry) in comparison to standard crosslinking, but requires only 30 seconds of UVA exposure.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating glaucoma in an individual in need thereof, comprising administering to the individual a therapeutically effective amount of riboflavin and an ultraviolet A (UVA) light exposure wherein the light has a wavelength of about 365 nm to about 475 nm, to the individual's peripapillary sclera, optic nerve, and lamina cribrosa, which results in crosslinking of collagen in the indiviudal's peripapillary sclera, thereby stiffening the individual's peripapillary sclera and treating the glaucoma in the individual.

2. The method of claim 1 wherein the riboflavin concentration is from about 0. 05% to about 0,2% and the light has a wavelength of about 430 nm to about 475 nm.

3. A method of treating glaucomatous optic neuropathy in an individual in need thereof, comprising administering to the individual a therapeutically effective amount of riboflavin and an ultraviolet A (UVA) light exposure wherein the light has a wavelength of about 365 nm to about 475 nm, to the individual's peripapillary sclera, optic nerve, and lamina cribrosa, which results in crosslinking of collagen in the individual's peripapillary sclera, thereby stiffening the individual's peripapillary sclera and treating the glaucomatous optic neuropathy in the individual.

4. The method of claim 3 wherein the riboflavin concentration is from about 0.05% to about 0.2% and the light has a wavelength of about 430 nm to about 475 nm.

5. A method of protecting all or a portion of the optic nerve fiber layer within the optic nerve/lamina cribrosa complex against the biomechanical effects of increased intraocular pressure from glaucoma in an individual in need thereof, comprising contacting the individual's peripapillary sclera, optic nerve, and lamina cribrosa with a therapeutically effective amount of riboflavin and an ultraviolet A (UVA) light exposure wherein the light has a wavelength of about 365 nm to about 475 nm, which results in the crosslinking of collagen in the individual's peripapillary sclera, thereby stiffening the individual's peripapillary sclera and protecting all or a portion of the optic nerve fiber layer within the optic nerve/lamina cribrosa against the increased intraocular pressure from glaucoma in the individual.

6. The method of claim 5 wherein the riboflavin concentration is from about 0.05% to about 0.2% and the light has at a wavelength of about 430 nm to about 475 nm.

7. A method of protecting all or a portion of the optic nerve fiber layer within the optic nerve/lamina cribrosa complex against the biomechanical effects of increased intraocular pressure from glaucoma in an individual in need thereof, comprising contacting the individual's peripapillary sclera with a therapeutically effective amount of glutaraldehyde which results in the crosslinking of collagen in the individual's peripapillary sclera, thereby stiffening the individual's peripapillary sclera and protecting all or a portion of the optic nerve fiber layer within the optic nerve/lamina cribrosa against the increased intraocular pressure from glaucoma in the individual.

8. A method of treating glaucoma in an individual in need thereof, comprising administering to the individual a therapeutically effective amount of glutaraldehyde to the individual's peripapillary sclera which results in crosslinking of collagen in the individual's peripapillary sclera, thereby stiffening the individual's peripapillary sclera and treating the glaucoma in the individual.

9. A method of treating glaucomatous optic neuropathy in an individual in need thereof, comprising administering to the individual a therapeutically effective amount of glutaraldehyde to the individual's peripapillary sclera which results in crosslinking of collagen in the individual's peripapillary sclera, thereby stiffening the individual's peripapillary sclera and treating the glaucomatous optic neuropathy in the individual.

* * * * *

UNITED STATES PATENT AND TRADEMARK OFFICE
CERTIFICATE OF CORRECTION

PATENT NO. : 8,580,789 B2
APPLICATION NO. : 12/593720
DATED : November 12, 2013
INVENTOR(S) : Ronald R. Krueger et al.

It is certified that error appears in the above-identified patent and that said Letters Patent is hereby corrected as shown below:

In the Claims

In Column 22, Claim 1, line 60, delete "indiviudal's" and insert --individual's--.

In Column 22, Claim 2, line 64, delete "0,2%" and insert --0.2%--.

In Column 23, Claim 6, line 27, delete "at".

Signed and Sealed this
Eighteenth Day of February, 2014

Michelle K. Lee
*Deputy Director of the United States Patent and Trademark Office*